(12) United States Patent
Dalko

(10) Patent No.: US 11,691,937 B2
(45) Date of Patent: *Jul. 4, 2023

(54) USE OF VANILLIN DERIVATIVES AS PRESERVING AGENTS, PRESERVING PROCESS, COMPOUNDS AND COMPOSITION

(71) Applicant: L'OREAL, Paris (FR)

(72) Inventor: Maria Dalko, Versailles (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/174,246

(22) Filed: Jun. 6, 2016

(65) Prior Publication Data

US 2017/0096381 A1   Apr. 6, 2017

Related U.S. Application Data

(62) Division of application No. 13/499,503, filed as application No. PCT/FR2010/051926 on Sep. 16, 2010, now abandoned.

(60) Provisional application No. 61/248,999, filed on Oct. 6, 2009.

(30) Foreign Application Priority Data

Oct. 1, 2009 (FR) .................................. 0956843
Nov. 17, 2009 (FR) .................................. 0958082

(51) Int. Cl.
  *A61K 8/35* (2006.01)
  *A61Q 19/00* (2006.01)
  *C07C 49/255* (2006.01)
  *A61K 47/10* (2017.01)

(52) U.S. Cl.
  CPC .............. *C07C 49/255* (2013.01); *A61K 8/35* (2013.01); *A61K 47/10* (2013.01); *A61Q 19/00* (2013.01); *A61K 2800/524* (2013.01)

(58) Field of Classification Search
  None
  See application file for complete search history.

(56) References Cited

U.S. PATENT DOCUMENTS

| | | | | |
|---|---|---|---|---|
| 6,287,583 B1 * | 9/2001 | Warren | ............... | A61K 8/0208 424/400 |
| 6,730,294 B1 | 5/2004 | Kritzler | | |
| 7,115,586 B2 * | 10/2006 | Loftsson | ............... | A61K 31/724 424/440 |
| 8,039,024 B2 * | 10/2011 | Reiner | .................. | A61K 31/05 424/725 |
| 2005/0195492 A1 | 9/2005 | Nishina et al. | | |
| 2008/0253976 A1 * | 10/2008 | Scott | .................... | A61K 8/0216 424/49 |

FOREIGN PATENT DOCUMENTS

| | | |
|---|---|---|
| EP | 1502594 A1 | 2/2005 |
| GB | 2354771 A | 4/2001 |
| IT | 001442 | 7/2002 |
| IT | 001571 | 7/2002 |
| JP | 60032705 A | 2/1985 |
| JP | 05 168401 A | 7/1993 |
| JP | 2002053408 A | 2/2002 |
| JP | 2003206239 * | 7/2003 |
| JP | 2004210656 A | 7/2004 |
| KR | 20020043073 A | 6/2002 |
| WO | WO-9323061 A1 | 11/1993 |
| WO | WO 2008/071027 A1 | 6/2008 |
| WO | WO 2009/019255 A2 | 2/2009 |

OTHER PUBLICATIONS

Lotion—Definition, Merriam_webster Dictionary, retrieved online on Jul. 6, 2017.*
Nanayama et al. Antibacterial actions of seasonings and spices on the viability of Vibrio parahaemolyticus, Jpn. J. Food Microbiol., 11(3), 173-178, 1994 (Year: 1994).*
M. Winter, "Odeur er constitution sur des homologues et analogues de la p-hydrooxyphenyl-1-butanone-3 (cetone de framboise)", Helvetica Chimica Acta (1961), 44, pp. 2110-2121.
Zhurnal Obshchey Khimii, 1949, 19, (3), 569-576.
Zhurnal Obshchey Khimii, 1949, 19, (4), 759-768.

(Continued)

*Primary Examiner* — Jennifer A Berrios
(74) *Attorney, Agent, or Firm* — Polsinelli PC

(57) ABSTRACT

The present invention relates to the use, in a cosmetic, dermatological or pharmaceutical composition, of at least one compound of formula (I):

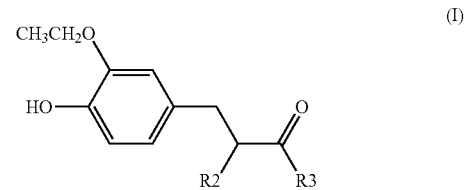

in which:
  R2 represents a hydrogen atom or a methyl or ethyl radical;
  R3 represents a linear C1-C12 alkyl radical, optionally substituted with a hydroxyl group; or a linear C2-C12 alkenyl radical, optionally substituted with a hydroxyl group;
as a preserving agent.

The invention also relates to certain novel compounds and to the cosmetic, dermatological or pharmaceutical compositions comprising them.

23 Claims, No Drawings

(56) References Cited

OTHER PUBLICATIONS

Kim et al., "Side-chain length is important for shogoals in protecting neuronal cells from β-amyloid insult," Bioorganic & Medicinal Chemistry Letters 14 (2004) 1287-1289.
SciFinder. Zingerone Structure, retrieved online on 9/92015.
JP2004-210656, Human Translation of Working Examples 1-8, Jun. 24, 2014.
"Ethylzingerone 'Hydroxyethoxyphenyl Butanone' (HEPB)"—Cosmetic Europe N° P98, The SCCS adopted this Opinion by written procedure on Apr. 7, 2017.

* cited by examiner

USE OF VANILLIN DERIVATIVES AS PRESERVING AGENTS, PRESERVING PROCESS, COMPOUNDS AND COMPOSITION

CROSS REFERENCE TO RELATED APPLICATIONS

This application is a Divisional of U.S. application Ser. No. 13/499,503 filed on Mar. 30, 2012, which is a National Phase filing under 35 U.S.C. § 371 of PCT/FR2010/051926 filed on Sep. 16, 2010; and this application claims priority to Application No. 0956843 filed in France on Oct. 1, 2009 and application Ser. No. 09/58,082 filed in France on Nov. 17, 2009 under 35 U.S.C. § 119; and claims the benefit of U.S. Provisional Application No. 61/248,999 filed on Oct. 6, 2009; the entire contents of all are hereby incorporated by reference.

The present invention relates to the use of vanillin derivatives especially as preserving agents in cosmetic, dermatological or pharmaceutical, or even nutraceutical or oral cosmetic compositions; the invention also relates to novel compounds that may be used in cosmetics, dermatology or pharmacy, or even nutraceutics or oral cosmetics, in particular as preserving agents, and also to compositions comprising these compounds.

It is common practice to introduce chemical preserving agents into cosmetic or dermatological compositions, these preserving agents being intended to combat the growth of microorganisms in these compositions, which would quickly make them unsuitable for use. It is in particular necessary to protect compositions against microorganisms capable of growing inside the composition, for example during production thereof, and also against those which the user might introduce therein while handling it, in particular when taking up products in jars with the fingers. Chemical preserving agents commonly used are in particular parabens, organic acids or formaldehyde-releasing compounds. However, these preserving agents have the drawback of causing irritation, in particular on sensitive skin, when they are present at relatively high levels. Moreover, in the interests of the environment, consumers are increasingly searching for environmentally friendly, in particular non-ecotoxic, preserving agents. In addition, the effectiveness of the preserving agents conventionally used is variable and their formulation can pose problems, in particular of incompatibility, or even of destabilization, of formulas, in particular of emulsions.

One object of the present invention is to propose novel preserving agents which in particular have a broad antimicrobial spectrum, at least as broad, or even broader, than that of the already existing compounds, and which do not have the drawbacks of the prior art, in particular which have specific physicochemical properties making it possible to protect cosmetic formulas against microbial contamination while at the same time being well tolerated.

A subject of the invention is therefore the use in a cosmetic, dermatological or pharmaceutical, even nutraceutical or oral cosmetic, composition, of at least one compound of formula (I):

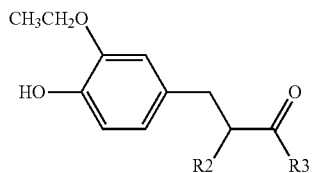

in which:
R2 represents a hydrogen atom or a methyl or ethyl radical;
R3 represents a linear C1-C12 alkyl radical (saturated), optionally substituted
with a hydroxyl group; or a linear C2-C12 alkenyl radical (C=C unsaturated), optionally substituted with a hydroxyl group,
as a preserving agent.

The term "preserving agent" is intended to mean a substance which is commonly added to a composition in order to preserve said composition with respect to a contaminating agent. Advantageously, the compounds of formula (I) according to the invention are used as an antimicrobial and/or antibacterial and/or antifungal agent.

Another subject of the invention is a process for preserving a cosmetic, dermatological, pharmaceutical, nutraceutical or oral cosmetic composition, characterized in that it consists in incorporating into the said composition at least one compound of formula (I).

Preferably, the compounds correspond to formula (I), in which:
R2 is chosen from among H and $CH_3$; better still R2=H and/or
R3 represents (i) a C1-C10 alkyl radical; (ii) a C2-C10 alkenyl radical, especially a radical —CH=CH—R4 with R4 representing a linear C1-C6 alkyl radical; or alternatively (iii) a hydroxyalkyl radical of structure —$CH_2$—CH(OH)—R5 with R5 representing a linear C1-C10 and preferably C4-C10 alkyl radical.

A mixture of compounds of formula (I) may, of course, be used.

Preferably, the composition does not comprise any preserving agents other than those of formula (I). In particular, the composition does not contain parabens.

Certain compounds of formula (I) are novel and also form a subject of the present invention; they are the compounds of formula (I') hereinbelow:

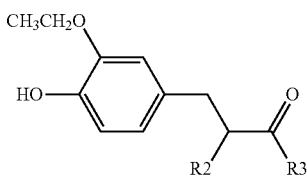

in which:
R2 represents a hydrogen atom, a methyl radical or an ethyl radical;
R3 represents a linear C2-C12 alkyl radical (saturated), optionally substituted with a hydroxyl group; or a linear C2-C12 alkenyl radical (C=C unsaturated), optionally substituted with a hydroxyl group.

Preferably, in formula (I'), R2 is chosen from among H and CH₃; better still R2=H. Preferably, in formula (I'), R3 represents (i) a C2-C10 alkyl radical; (ii) a C2-C10 alkenyl radical, especially a radical —CH=CH—R4 with R4 representing a linear C1-C6 alkyl radical; or alternatively (iii) a hydroxyalkyl radical of structure —CH₂—CH(OH)—R5 with R5 representing a linear C1-C10 and preferably C4-C10 alkyl radical.

Mention may be made in particular of the following compounds of formula (I):

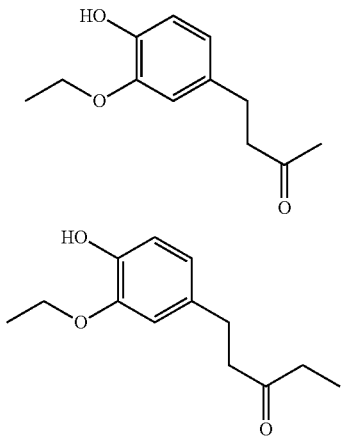

The cosmetic, dermatological or pharmaceutical compositions comprising at least one compound of formula (I) or of formula (I') also form a subject of the present invention.

The compounds of formula (I) can be readily prepared by those skilled in the art on the basis of their general knowledge. Mention may be made especially of the following bibliographic references: J. Asian Natural Products Research, 2006, 8(8), 683-688; Helv. Chimica Acta, 2006, 89(3), 483-495; Chem. Pharm. Bull., 2006, 54(3), 377-379; and Bioorg. J. Med. Chem. Lett., 2004, 14(5), 1287-1289.

They may thus be prepared from ethylvanillin, in the following manner:

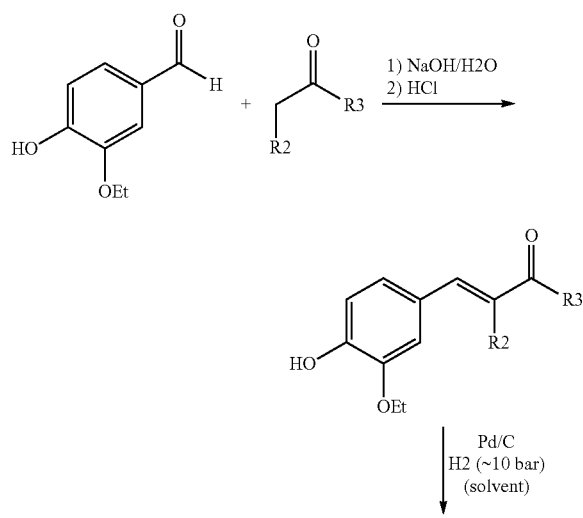

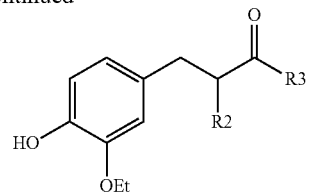

The compounds of formula (I), alone or as a mixture, may be used in a proportion of from 0.01% to 5% by weight and in particular 0.1% to 2.5% by weight, relative to the weight of the composition, in cosmetic, dermatological or pharmaceutical compositions.

The cosmetic, dermatological or pharmaceutical compositions moreover comprise a cosmetically, dermatologically or physiologically acceptable medium, i.e. a medium that is compatible with keratin materials such as facial or bodily skin, the lips, the hair, the eyelashes, the eyebrows and the nails.

The compositions according to the invention may be in any galenical form conventionally used, in particular for topical application, and in particular in the form of aqueous or aqueous/alcoholic solutions, of oil-in-water (O/W), water-in-oil (W/O) or multiple (triple: W/O/W or O/W/O) emulsions, of aqueous gels or of dispersions of a fatty phase in an aqueous phase using spherules, it being possible for these spherules to be polymeric nanoparticles, such as nanospheres and nanocapsules, or lipid vesicles of ionic and/or nonionic type (liposomes, niosomes or oleosomes), of nanoemulsions, or of thin films. These compositions are prepared according to the usual methods.

The compositions according to the invention may be more or less fluid and may have the appearance of a white or coloured cream, an ointment, a milk, a lotion, a serum, a paste or a foam. They can optionally be applied to the skin in the form of an aerosol. They can also be in solid form, for example in the form of a stick.

The composition according to the invention may in particular be in the form of:
  a product for making up the skin of the face, body or lips;
  an aftershave gel or lotion;
  a hair-removing cream;
  a body hygiene composition such as a shower gel or a shampoo;
  a pharmaceutical composition;
  a solid composition such as a soap or a cleansing bar;
  an aerosol composition also comprising a pressurized propellent;
  a hair-setting lotion, a hair-styling cream or gel, a dyeing composition, a hair-restructuring lotion, a permanent-wave composition, a lotion or a gel for combating hair loss; or
  a composition for oro-dental use.

The physiologically acceptable medium in which the compounds can be used, and also its constituents, their amount, the galenical form of the composition and the method for preparing said composition may be chosen by those skilled in the art on the basis of their general knowledge as a function of the type of composition desired.

In particular, the composition may comprise any fatty substance normally used in the field of application envisaged. Mention may in particular be made of silicone fatty substances such as silicone oils, gums and waxes and also nonsilicone fatty substances such as oils, pastes and waxes of plant, mineral, animal and/or synthetic origin. The oils may be volatile or non-volatile.

Among the silicone oils, mention may be made of volatile or non-volatile polydimethylsiloxanes (PDMSs) with a linear or cyclic silicone chain, which are liquid or pasty at room temperature, in particular cyclopolydimethylsiloxanes such as cyclohexasiloxane; polydimethylsiloxanes comprising alkyl, alkoxy or phenyl groups, which are pendent or at the end of a silicone chain, these groups containing from 2 to 24 carbon atoms; phenylsilicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes.

Among the hydrocarbon-based oils of plant origin, mention may be made of liquid triglycerides of fatty acids containing from 4 to 10 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, castor oil, avocado oil, caprylic/capric acid triglycerides, jojoba oil and shea butter oil.

Mention may also be made, as a fatty substance that can be used, of:
  fatty acids containing from 8 to 32 carbon atoms;
  synthetic esters and ethers, in particular of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, for instance purcellin oil, isononyl isononanoate, isopropyl myristate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, fatty alcohol heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;
  linear or branched hydrocarbons of mineral or synthetic origin, such as volatile or non-volatile liquid paraffins, and derivatives thereof, petroleum jelly, polydecenes, and hydrogenated polyisobutene such as Parleam oil;
  fatty alcohols containing from 8 to 26 carbon atoms, for instance cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol.

The composition may also comprise an aqueous medium that comprises water, an aqueous-alcoholic medium containing a C2-C6 alcohol such as ethanol or isopropanol, or an organic medium comprising standard organic solvents such as C2-C6 alcohols, in particular ethanol and isopropanol, glycols such as propylene glycol, and ketones.

The composition according to the invention may also comprise the adjuvants that are customary in the cosmetic and dermatological fields, such as thickeners, emulsifiers, surfactants, gelling agents, active cosmetic agents, fragrances, fillers, dyestuffs, moisturizers, vitamins and polymers. The amounts of these various adjuvants are those conventionally used in the fields under consideration, for example from 0.001% to 20% of the total weight of the composition. These adjuvants and the concentrations thereof must be such that they are not detrimental to the advantageous properties of the compounds according to the invention.

The pH of the compositions according to the invention, when they comprise at least one aqueous phase (for example aqueous solutions, emulsions), is preferably between 4 and 9, preferably between 4 and 7, advantageously between 5 and 6.

The invention is illustrated in greater detail in the following exemplary embodiments.

EXAMPLE 1

Determination of the Antimicrobial Activity of a Compound According to the Invention The antimicrobial efficacy of a compound of formula (I) was evaluated via the Challenge Test or artificial contamination method.

Compound Tested:

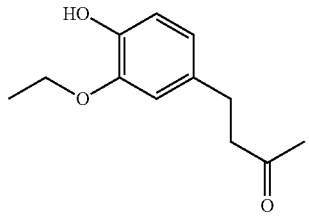

Protocol

The method of the challenge test consists of an artificial contamination of the sample with collection microbial strains (bacteria, yeasts and moulds) and evaluation of the number of revivable microorganisms seven days after the inoculation.

In order to demonstrate the effect of the compounds of formula (I) the antimicrobial activity of a cosmetic formula containing, respectively, 2% of a compound according to the invention was compared with the same formula alone (control), after inoculation with about $10^6$ cfu (colony-forming units)/gram of cosmetic formula.

Cosmetic Formula (Weight %)

| | |
|---|---|
| sorbitan tristearate (Span 65 V ® from Croda) | 0.9% |
| polyethylene glycol stearate (40 OE) (Myrj 52 P ® from Croda) | 2.0% |
| glyceryl mono-distearate (36/64)/potassium stearate mixture | 3.0% |
| fatty acids of plant origin (53/44/3 stearic acid/palmitic acid/myristic acid) | 1.0% |
| cetyl alcohol | 3.8% |
| myristyl myristate | 2.0% |
| cyclopentasiloxane | 5.0% |
| fillers | 0.8% |
| glycerol | 3.0% |
| hydrogenated isoparaffin | 7.2% |
| white petroleum jelly | 4.0% |
| water | qs 100% |

Microorganism Cultures 5 pure microorganism cultures are used.

| MICROORGANISMS | Subculturing medium | T° | ATCC |
|---|---|---|---|
| Escherichia coli (Ec) | Trypto-casein soya | 35° C. | 8739 |
| Enterococcus faecalis (Ef) | Trypto-casein soya | 35° C. | 33186 |

-continued

| MICROORGANISMS | Subculturing medium | T° | ATCC |
|---|---|---|---|
| *Pseudomonas aeruginosa* (Pa) | Trypto-casein soya | 35° C. | 19429 |
| *Candida albicans* (Ca) | Sabouraud | 35° C. | 10231 |
| *Aspergillus niger* (An) | Malt | 35° C. | 6275 |

ATCC = American Type Culture Collection

The gram-negative bacteria (*Escherichia coli* and *Pseudomonas aeruginosa*), gram-positive bacteria (*Enterococcus faecalis*), yeast (*Candida albicans*) and mould (*Aspergillus niger*) are seeded in the subculturing medium, respectively, the day before the inoculation for the bacteria and the yeast, and five days before the inoculation for the mould.

On the day of inoculation:
- a suspension in Tryptone salt diluent is prepared, respectively, for the bacteria and the yeast, so as to obtain in a spectrophotometer a suspension with an optical density of between 35% and 45% transmitted light at 544 nm;
- for the mould, the spores are collected by washing the agar with 6 to 7 ml of harvesting solution and the suspension is recovered in a sterile tube or flask.

After homogenizing the microbial suspension, 0.2 ml of inoculum is introduced into each pill bottle (the suspensions are used pure: between $1 \times 10^8$ and $3 \times 10^8$ cfu per ml) and the microbial suspension in the 20 g of product (=cosmetic formula) is homogenized thoroughly using a spatula.

The content of microorganisms present in the product corresponds after homogenization to a concentration of $10^6$ microorganisms per gram of product, i.e. inoculation to 1% of an inoculum containing $10^8$ microorganisms per ml. After 7 days of contact time between the microorganisms and the product at 22° C.±2° C. and in darkness, decimal dilutions are performed and the number of revivable microorganisms remaining in the product is counted.

Results

| | | No. of cfu/gram of product at T7 days | | | | |
|---|---|---|---|---|---|---|
| | Content | E. coli | P. aeruginosa | E. faecalis | C. albicans | A. niger |
| Compound | 2% | <200 | <200 | <200 | <200 | $3.4 \times 10^5$ |

<200 cfu: sensitivity threshold of the method

EXAMPLE 2

An emulsion is prepared, comprising (weight %):

| | |
|---|---|
| sorbitan tristearate (Span 65 V ® from Croda) | 0.9% |
| polyethylene glycol stearate (40 OE) (Myrj 52 P ® from Croda) | 2% |
| glyceryl mono-distearate (36/64)/potassium stearate mixture | 3% |
| fatty acids of plant origin (53/44/3 stearic acid/palmitic acid/myristic acid) | 1% |
| glycerol | 3% |
| cyclopentasiloxane | 5% |
| hydrogenated isoparaffin | 7.2% |
| white petroleum jelly | 4% |
| cetyl alcohol | 4% |
| myristyl myristate | 2% |
| fillers | 0.8% |
| compound tested in Example 1 | 2% |
| water | qs 100% |

EXAMPLE 3

An O/W emulsion is prepared, comprising (weight %):

| | |
|---|---|
| sodium hydroxide | 0.03% |
| liquid petroleum jelly | 10% |
| 2-ethylhexyl palmitate | 10% |
| acrylic acid/stearyl methacrylate copolymer polymerized in an ethyl acetate/cyclohexane mixture | 0.1% |
| glycerol | 5% |
| mixture of cetylstearyl glucoside and of cetyl and stearyl alcohols (12/46/42) | 2.45% |
| compound tested in Example 1 | 2% |
| microbiologically clean deionized water | qs 100% |

EXAMPLE 4

A lotion is prepared, comprising (weight %):

| | |
|---|---|
| allantoin | 0.05% |
| sodium chloride | 0.09% |
| citric acid | qs pH 7 ± 0.2 |
| cornflower water | 1% |
| hexylene glycol (2-methyl-2,4-pentanediol) | 1% |
| glycerol | 5% |
| sodium N-cocoylamidoethyl-N-ethoxycarboxymethyl glycinate | 1.1% |
| sodium/magnesium lauryl ether sulfate (80/20) 40 OE (52% SM) | 0.45% |
| compound tested in Example 1 | 1.5% |
| microbiologically clean deionized water | qs 100% |

What is claimed is:

1. A process for preserving a composition, which comprises incorporating an effective preserving amount into the said composition of a compound of the following formula

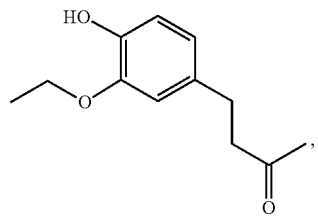

wherein said compound is present in an amount of from 0.01% to 5% by weight, relative to the weight of the composition.

2. The process according to claim 1, wherein said compound is present in an amount of from 0.01% to 2.5% by weight, relative to the weight of the composition.

3. The process according to claim 1, wherein the composition does not contain any preserving acting agent in addition to said compound.

4. The process according to claim 1, wherein the composition does not contain a paraben.

5. The process according to claim 1, wherein the composition is in the form of a product for making up the skin of the face, body or lips; an aftershave gel or lotion; a hair-removing cream; a body hygiene composition; a pharmaceutical composition; a solid composition; an aerosol composition also comprising a pressurized propellant; a hair-setting lotion, a hair-styling cream or gel, a dyeing composition, a hair-restructuring lotion, a permanent-wave composition, a lotion or a gel for combating hair loss; or a composition for oro-dental use.

6. The process according to claim 1, wherein the composition comprises a physiologically acceptable medium which comprises at least one ingredient selected from the group consisting of silicone fatty substances selected from the group consisting of silicone oils, gums and waxes; non-silicone fatty substances selected from the group consisting of oils, pastes and waxes of plant, mineral, animal and/or synthetic origin; and wherein the composition optionally further comprises an active cosmetic agent.

7. The process according to claim 1, wherein the composition comprises a physiologically acceptable medium comprising at least one ingredient selected from the group consisting of silicone fatty substances, non-silicone fatty substances, glycols, ketones, thickeners, emulsifiers, surfactants, gelling agents, fragrances, fillers, dyestuffs, moisturizers, vitamins and polymers.

8. The process according to claim 1, wherein said composition comprises at least one aqueous phase and has a pH of 4 to 9.

9. The process according to claim 1, wherein said composition comprises at least one aqueous phase and has a pH of 4 to 7.

10. The process according to claim 1, wherein said composition comprises at least one aqueous phase and has a pH of 5 to 6.

11. The process according to claim 1, which comprises preserving said composition against at least one contaminating agent selected from the group consisting of bacteria, yeast and mould.

12. The process according to claim 5, wherein said body hygiene composition is a shower gel or a shampoo.

13. The process according to claim 5, wherein said solid composition is a soap or a cleansing bar.

14. The process according to claim 1, wherein said composition does not contain any ester having the structure $R^1COOR^2$ in which $R^1$ represents a fatty acid residue containing from 8 to 29 carbon atoms and $R^2$ represents a branched or unbranched hydrocarbon-based chain containing from 3 to 30 carbon atoms.

15. The process according to claim 1, wherein said composition exhibits less than 200 cfu/gram of *E. coli, P. aeruginosa, E. faecalis, C. albicans*, and/or *A. niger* after 7 days when inoculated with about $10^6$ cfu/gram of the *E. coli, P. aeruginosa, E. faecalis, C. albicans*, and/or *A. niger* and maintained at 22° C.±2° C.

16. A process for preserving a composition exposed to at least one of the group consisting of bacteria, yeasts and molds which comprises incorporating an effective preserving amount into the said composition of a compound of the following formula

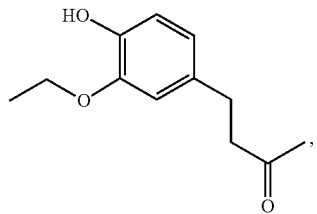

wherein said compound is present in an amount of from 0.01% to 5% by weight, relative to the weight of the composition.

17. The process according to claim 16, wherein said composition does not contain any ester having the structure $R^1COOR^2$ in which $R^1$ represents a fatty acid residue containing from 8 to 29 carbon atoms and $R^2$ represents a branched or unbranched hydrocarbon-based chain containing from 3 to 30 carbon atoms.

18. The process according to claim 17, wherein said composition exhibits less than 200 cfu/gram of *E. coli, P. aeruginosa, E. faecalis, C. albicans*, and/or *A. niger* after 7 days when inoculated with about $10^6$ cfu/gram of the *E. coli, P. aeruginosa, E. faecalis, C. albicans*, and/or *A. niger* and maintained at 22° C.±2° C.

19. The process according to claim 17, wherein the composition does not contain any preserving acting agent in addition to said compound.

20. The process according to claim 1, wherein said composition exhibits less than 200 cfu/gram of *E. coli, P. aeruginosa, E. faecalis, C. albicans*, and/or *A. niger* after 7 days when inoculated with about $10^6$ cfu/gram of the *E. coli, P. aeruginosa, E. faecalis, C. albicans*, and/or *A. niger* and maintained at 22° C.±2° C.

21. The process according to claim 16, wherein the composition is in the form of a product for making up the skin of the face, body or lips; an aftershave gel or lotion; a hair-removing cream; a body hygiene composition; a pharmaceutical composition; a solid composition; an aerosol composition also comprising a pressurized propellant; a hair-setting lotion, a hair-styling cream or gel, a dyeing composition, a hair-restructuring lotion, a permanent-wave composition, a lotion or a gel for combating hair loss.

22. The process according to claim 1, wherein the composition is in the form of a product for making up the skin of the face, body or lips; an aftershave gel or lotion; a hair-removing cream; a body hygiene composition; a pharmaceutical composition; a solid composition; an aerosol composition also comprising a pressurized propellant; a hair-setting lotion, a hair-styling cream or gel, a dyeing composition, a hair-restructuring lotion, a permanent-wave composition, a lotion or a gel for combating hair loss.

23. The process according to claim 22, wherein said composition does not contain any ester having the structure $R^1COOR^2$ in which $R^1$ represents a fatty acid residue containing from 8 to 29 carbon atoms and $R^2$ represents a branched or unbranched hydrocarbon-based chain containing from 3 to 30 carbon atoms.

\* \* \* \* \*